United States Patent [19]

Lee

[11] 4,156,304

[45] May 29, 1979

[54] BIOMEDICAL ULTRASONOSCOPE

[75] Inventor: Robert D. Lee, San Mateo, Calif.

[73] Assignee: The United States of America as represented by the Administrator of the National Aeronautics and Space Administration, Washington, D.C.

[21] Appl. No.: 728,369

[22] Filed: Sep. 30, 1976

[51] Int. Cl.$^2$ .............................................. A61B 5/00
[52] U.S. Cl. ..................................... 128/660; 73/626
[58] Field of Search ........................ 128/2 V, 205 Z; 73/67.7, 67.8 R, 67.8 S, 626, 631, 620

[56] References Cited

U.S. PATENT DOCUMENTS

| | | | |
|---|---|---|---|
| 3,274,821 | 9/1966 | Weighart | 73/67.8 |
| 3,292,018 | 12/1966 | Clynes | 128/2 V |
| 3,554,013 | 1/1971 | Berg | 73/67.7 |
| 3,881,466 | 5/1975 | Wilcox | 73/626 X |
| 3,884,325 | 5/1975 | Cowles | 73/632 X |
| 3,942,358 | 3/1976 | Pies | 73/67.7 |
| 4,016,862 | 4/1977 | Lancee et al. | 73/67.8 R X |

*Primary Examiner*—Dalton L. Truluck
*Assistant Examiner*—Michael H. Thaler
*Attorney, Agent, or Firm*—Darrell G. Brekke; John R. Manning; Armand McMillan

[57] ABSTRACT

The combination of a "C" mode scan electronics in a portable, battery powered biomedical ultrasonoscope having "A" and "M" mode scan electronics, the latter including a clock generator for generating clock pulses, a cathode ray tube having X, Y and Z axis inputs, a sweep generator connected between the clock generator and the X axis input of the cathode ray tube for generating a cathode ray sweep signal synchronized by the clock pulses, and a receiver adapted to be connected to the Z axis input of the cathode ray tube. The "C" mode scan electronics comprises a plurality of transducer elements arranged in a row and adapted to be positioned on the skin of the patient's body for converting a pulsed electrical signal to a pulsed ultrasonic signal, radiating the ultrasonic signal into the patient's body, picking up the echoes reflected from interfaces in the patient's body and converting the echoes to electrical signals; a plurality of transmitters, each transmitter being coupled to a respective transducer for transmitting a pulsed electrical signal thereto and for transmitting the converted electrical echo signals directly to the receiver, a sequencer connected between the clock generator and the plurality of transmitters and responsive to the clock pulses for firing the transmitters in cyclic order; and a staircase voltage generator connected between the clock generator and the Y axis input of the cathode ray tube for generating a staircase voltage having steps synchronized by the clock pulses.

3 Claims, 9 Drawing Figures

BIOMEDICAL ULTRASONOSCOPE

ORIGIN OF THE INVENTION

The invention described herein was made by an employee of the United States Government and may be manufactured and used by or for the Government for governmental purposes without the payment of any royalties thereon or therefor.

BACKGROUND OF THE INVENTION

1. Field of the Invention

The present invention relates generally to ultrasonic devices of the pulse-echo type, and more particularly to such devices which are suited for examination of the interior of a patient's body for non-invasive medical diagnosis.

2. Description of the Prior Art

Ultrasonic pulse-echo systems have heretofore been proposed for the examination of the interior of a patient's body. The present echocardioscope, echocardiagraph, echoencephalograph, or ultrasonoscope displays inter-bio-organs with a single ultrasonic element transducer by non-invasive techniques and with the aid of mechanical and/or electrical devices to provide several different types of displays. These include mechanical linear, arc hand held sector, compound scans, and their respective types of displays. The most common ultrasonic diagnostic instrument in use is the echocardiograph which utilizes a hand-held single ultrasonic element transducer for non-invasive examination of heart patients. The single ultrasonic element transducer echocardiograph provides "A" mode and "M" mode oscilloscope (CRT) visual displays.

None of the known biomedical ultrasonoscopes is capable of a selection of visual displays including "C" mode scan as well as the common "A" and "M" modes. Furthermore, conventional biomedical ultrasonoscopes are large and bulky, and incapable of portable, battery powered operation.

BRIEF SUMMARY OF THE INVENTION

It is therefore one object of the present invention to provide an improved biomedical ultrasonoscope.

It is another object to provide an improved biomedical ultrasonoscope which permits a thorough diagnostic examination while being as simple and as compact as possible.

It is yet another object to provide an improved biomedical ultrasonoscope incorporating "C" mode, "A" mode, and "M" mode scans while being as simple and as compact as possible.

The objects of the present invention are achieved by the combination of "C" mode scan means in a biomedical ultrasonoscope having "A" and "M" mode scan means, the latter including a clock generator for generating clock pulses, a cathode ray tube having X, Y, and Z axis inputs, a sweep generator connected between the clock generator and the X axis input of the cathode ray tube for generating a cathode ray sweep signal synchronized by the clock pulses, and a receiver adapted to be connected to the Z axis input of the cathode ray tube. The "C" mode scan means comprises transducer means including a plurality of transducer elements arranged in a row and adapted to be positioned on the skin of the patient's body for converting a pulsed electrical signal to a pulsed ultrasonic signal, radiating the ultrasonic signal into the patient's body, picking up the echos reflected from interfaces in the patient's body and converting the echos to electrical signals; a plurality of transmitters, each transmitter being coupled to a respective transducer for transmitting a pulsed electrical signal thereto and for transmitting the converted electrical echo signals directly to the receiver; sequencer means connected between the clock generator and the plurality of transmitters and responsive to the clock pulses for firing the transmitters in cyclic order; and a staircase voltage generator connected between the clock generator and the Y axis input of the cathode ray tube for generating a staircase voltage having steps synchronized by the clock pulses.

An important feature of the invention is the use of a single or common receiver, whereas some "C" mode display instruments utilize separate receivers for each transducer in the array.

Another important feature of the invention is that it permits the use of COS/MOS integrated logic circuit components so as to minimize power consumption.

The foregoing as well as other objects, features, and advantages of the present invention will become more apparent from the following detailed description taken in conjunction with the appended drawings.

BRIEF DESCRIPTION OF THE DRAWINGS

FIGS. 9(a) to (e) is a second series of waveforms produced at various points in the schematic circuit diagram of FIG. 6 and 7.

DESCRIPTION OF THE PREFERRED EMBODIMENT

Figure 1:
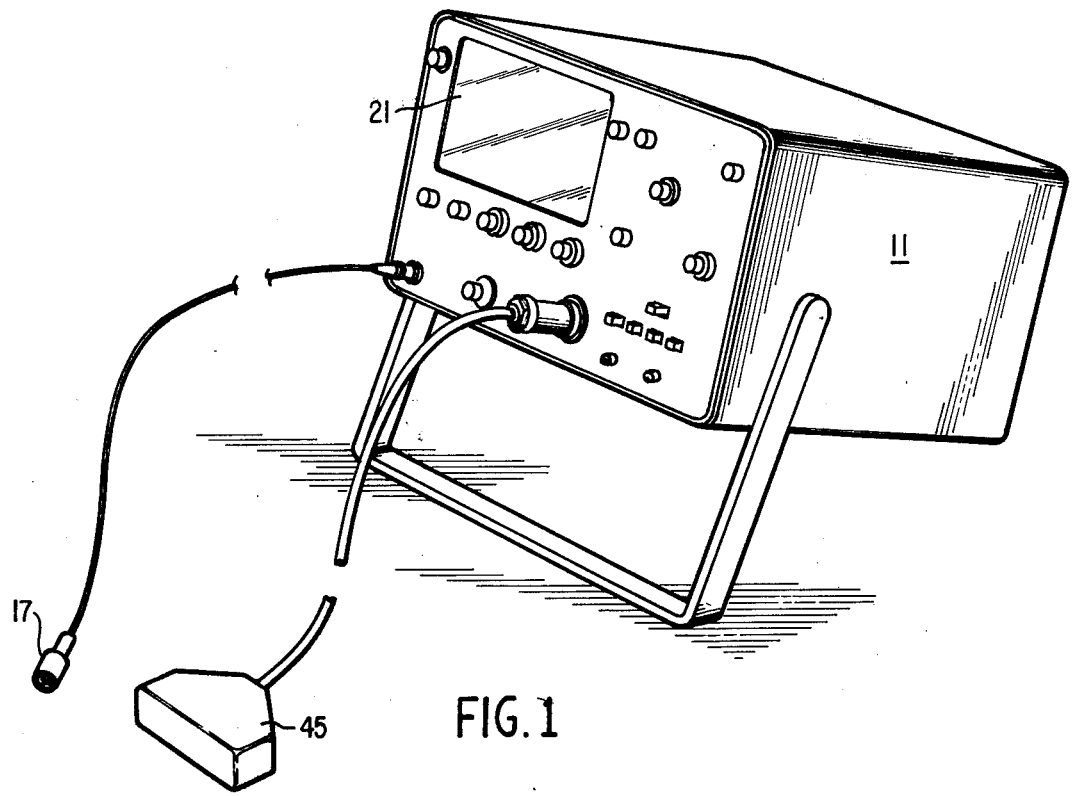
FIG. 1 is an isometric view of the exterior structure of the ultrasonoscope of this invention.
Figure 2:
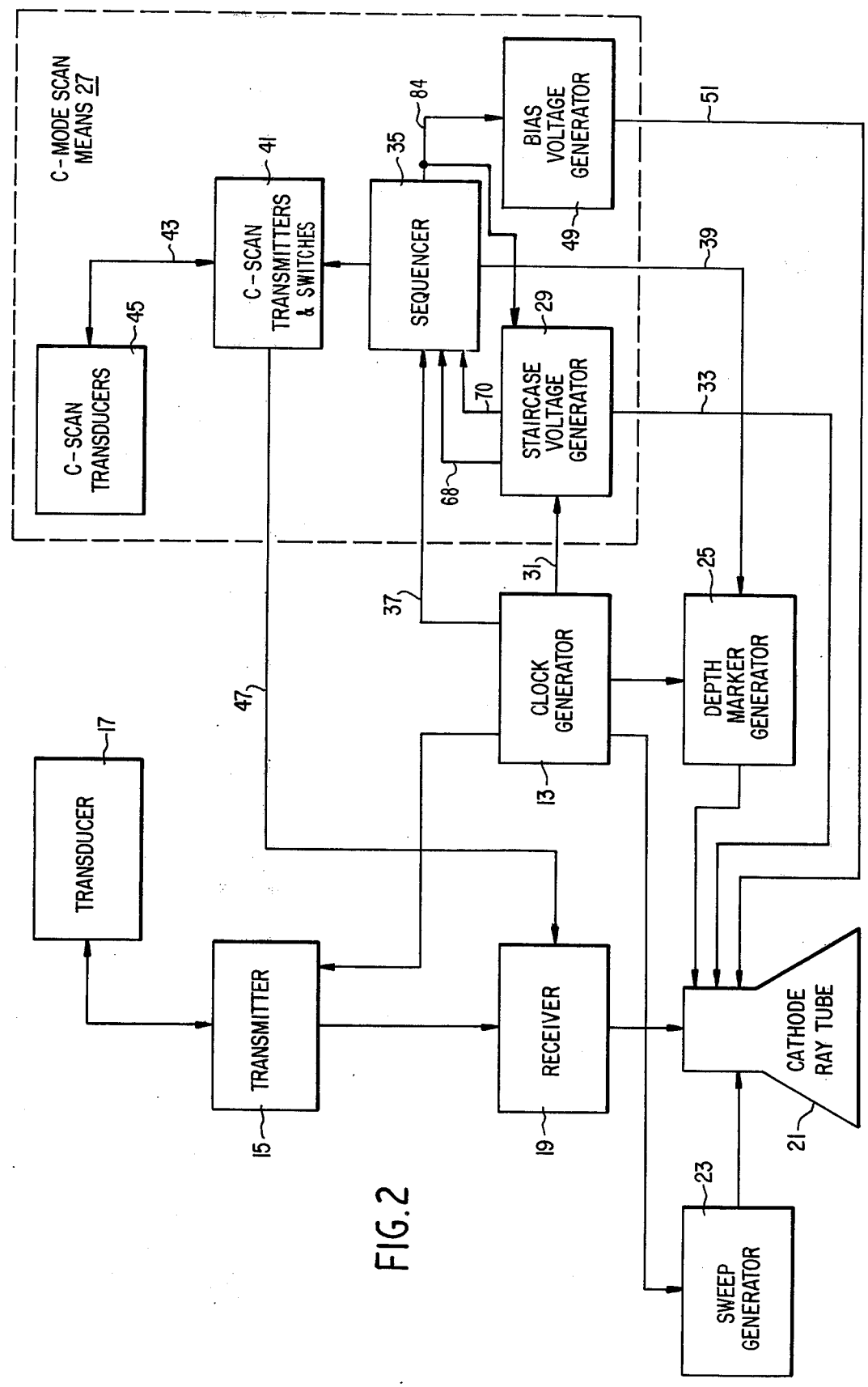
FIG. 2 is a block diagram of a preferred embodiment of the ultrasonoscope of this invention.

FIG. 1 illustrates, in isometric view, the exterior structure of the portable, battery powered ultrasonoscope 11 of the invention which is provided for the examination of the interior of a patient's body. FIG. 2 illustrates the invention in block form. A master clock generator 13 generates a repetitive clock pulse which is fed as a trigger pulse to a transmitter 15. The transmitter 15 transmits an electrical pulse to an ultrasonic transducer 17 which is positioned on the skin of the patient's body. The transducer 17 converts the electrical signal to an ultrasonic pulse which it radiates into the patient's body from the end of the transducer. Echoes are reflected from the surface of the body and from interfaces in the body. The echoes are picked up by the transducer 17 and converted to electrical echoes signals. The electrical echo signals are applied to a receiver 19. The receiver 19 receives the electrical echo signals and feeds them to a cathode ray tube 21. The signal generated by the master clock generator 13 is also fed as a trigger pulse to a time-base sweep generator 23. The time-base sweep generator 23 generates a sawtooth time-base sweep signal. The time-base sweep signal is applied to the X axis input of the cathode ray tube 21 to horizontally deflect a spot of light produced on the screen of the cathode ray tube synchronously with the pulsing of the transducer 17. "A" mode scan and "M" mode scan are combined in the ultrasonoscope. In "A" mode, the signal from the receiver 19 is applied to the Y axis input of the cathode ray tube 21. In "M" mode the signal from the receiver 19 is applied to the Z axis input of the cathode ray tube 21.

Figure 3:
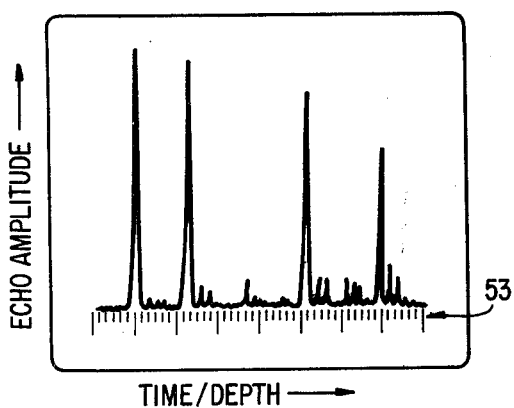
FIG. 3 shows the representation obtained by display of the echo signals on the screen of the cathode ray tube with "A" mode scan.

FIG. 3 illustrates "A" mode scan wherein the echoes are presented as vertical deflections of the trace or "pips" on the screen, and since the time delay between a transmitted pulse and the received echo depends on the distance between the transducer to the reflecting interface, the depth of the reflecting interface from the end of the transducer is represented along the X axis.

Figure 4:
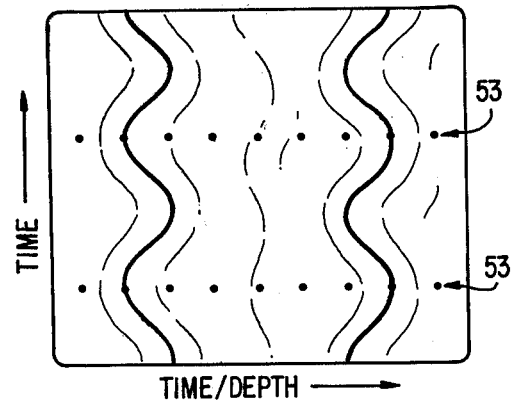
FIG. 4 shows the representation obtained by display of the echo signals on the screen of the cathode ray tube with "M" mode scan.

FIG. 4 illustrates "M" mode scan wherein the echoes are represented as a brightening or intensity modulation of the time-base trace and the time-base is swept at right angles to its direction so as to plot the position of an interface which is moving. Elapsed time is represented along the Y axis, and the depth of the reflecting interface from the end of the transducer is represented along the X axis.

The signal generated by the master clock generator 13 is also fed to a depth marker generator 25. The depth marker generator 25 generates repetitive pulses which are fed to the Y axis input of the cathode ray tube 21 to provide depth markers along the base line of the display. In FIGS. 3 and 4, depth markers are denoted by the numeral 53.

In accordance with the present invention, the ultrasonoscope is further provided with "C" mode scan means outlined by the broken line 27.

In "C" mode, the repetitive clock pulses generated by the master clock generator 13 are fed as trigger pulses to a staircase voltage generator 29 over connections represented by lead 31. The staircase voltage generator 29 generates a staircase voltage signal whose steps are in sync with the clock pulses. The staircase signal is applied over connections represented by lead 33 to the Y axis input of the cathode ray tube 21. The signal generated by the master clock generator 13 is also fed to a sequencer 35 over lead 37. The sequencer 35 is provided with a plurality of output terminals whose number (N+4) where N is a positive integer, is determined by the desired resolution of the display, and may amount to 24 for example. The sequencer 35 is set by the clock pulse to initiate a trigger pulse at each one of its out-put terminals in time sequence. The second output terminal and the second-from-last output terminal are connected to the depth marker generator 25 over connections represented by lead 39. The second and second-from-last trigger pulses in the sequence cause display of the depth markers at the bottom and top of the screen of the cathode ray tube. A plurality 41 of transmitters, N in number, are connected respectively to the third through third-from-last output terminals of the sequencer 35. Each of the next N trigger pulses after the first two in the sequence fire the transmitters 41 in cyclic order. Each transmitter transmits an electrical pulse over connections represented by lead 43 to a respective one of an array of N ultrasonic transducers 45 arranged in a row and positioned on the skin of the patient's body. The respective transducer converts electrical signal to an ultrasonic pulse which is radiated into the patient's body from the end of the transducer. The echoes are picked up by the transducer and converted to electrical echo signals. The electrical echo signals are applied to the receiver 19 over connections represented by lead 47. The last output terminal of the sequencer is connected to a bias voltage generator 49. The last trigger pulse in the sequence causes the bias voltage generator 49 to generate a bias voltage for offsetting the vertical position of the staircase voltage half a raster line from that of the previous frame on the screen of the cathode ray tube 21. The bias voltage signal is applied over connections represented by lead 51 to the Y axis input of the cathode ray tube.

In "C" mode, the receiver signal is applied to the Z axis input of the cathode ray tube.

Figures 5, 9:
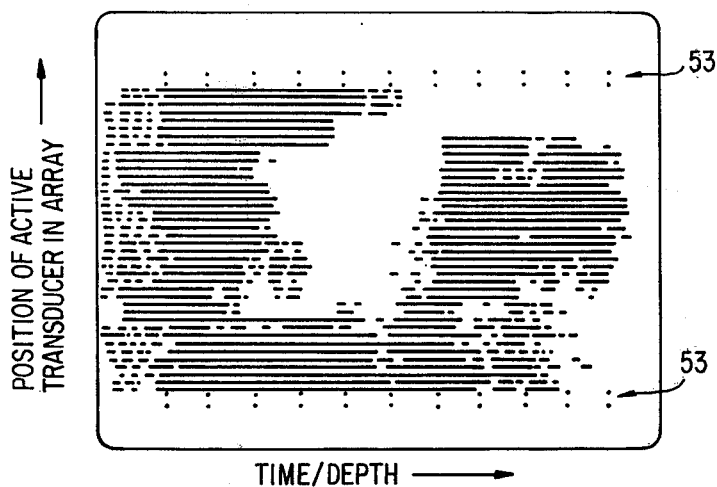
FIG. 5 shows the representation obtained by display of the echo signals on the screen of the cathode ray tube with "C" mode scan.

FIG. 5 illustrates "C" mode scan wherein the echoes are represented as a brightening or intensity modulation of the cathode ray. The vertical position of the cathode ray corresponds at any time with the position of the active transducer in the array. The depth of the reflecting interface from the plane of the transducer is represented along the X axis. The number of horizontal lines in the frame is selected as twice the number of transducers plus two extra lines at the top and bottom for depth markers. The bias voltage applied to the Y axis input produces the visual effect of having twice the number of ultrasonic transducers in the array, thereby enhancing the display. Depth markers are denoted by the numeral 53. The representation obtained on the screen of the cathode ray tube provides a two dimensional or cross-sectional image of anatomical organs or structures or the like, in which all displacements, for instance, of the heart wall, can be observed.

Figure 6:
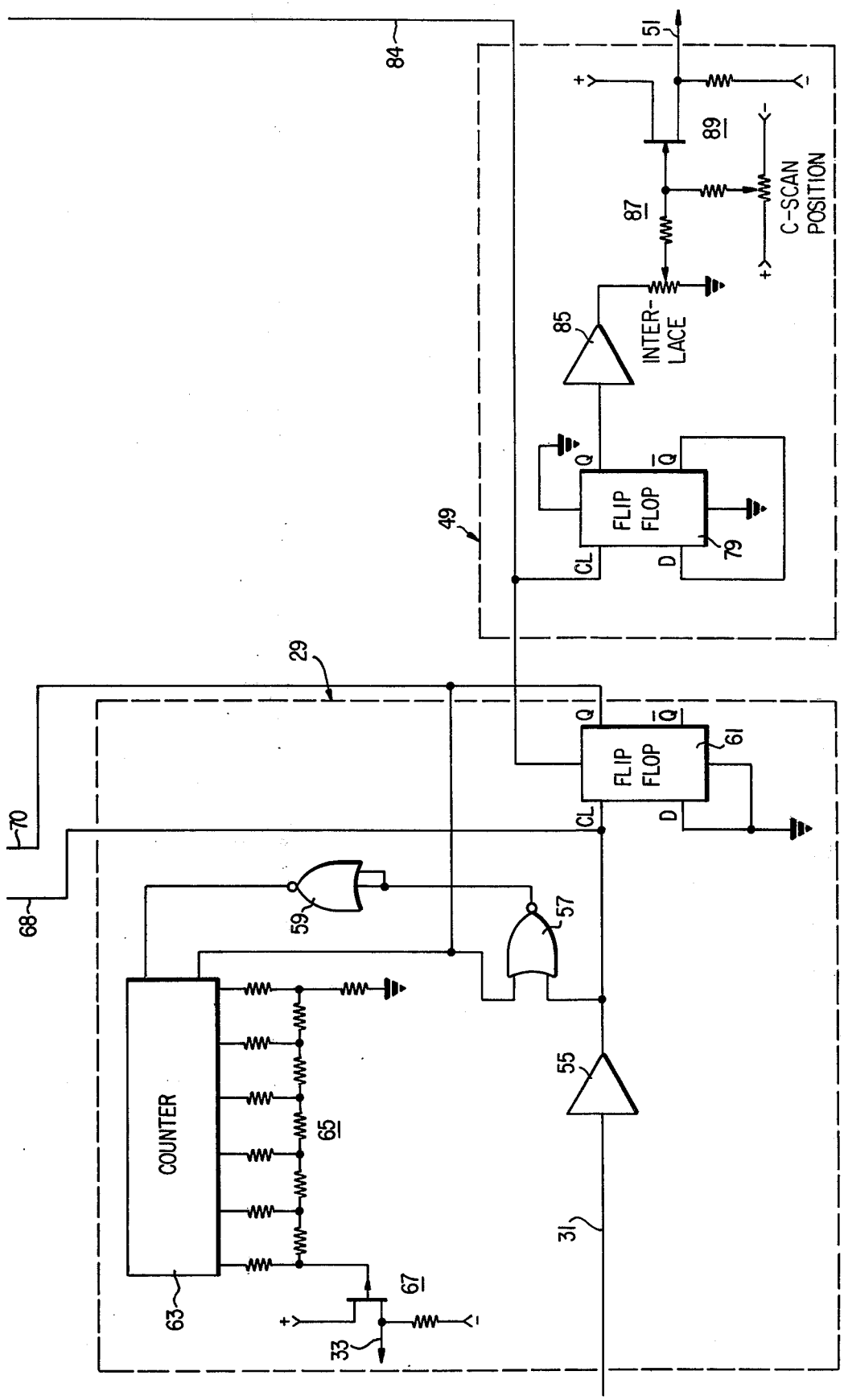
FIGS. 6 and 7 collectively show a schematic circuit diagram of the "C" mode scan means of the preferred embodiment of the ultrasonoscope of this invention.
Figure 7:
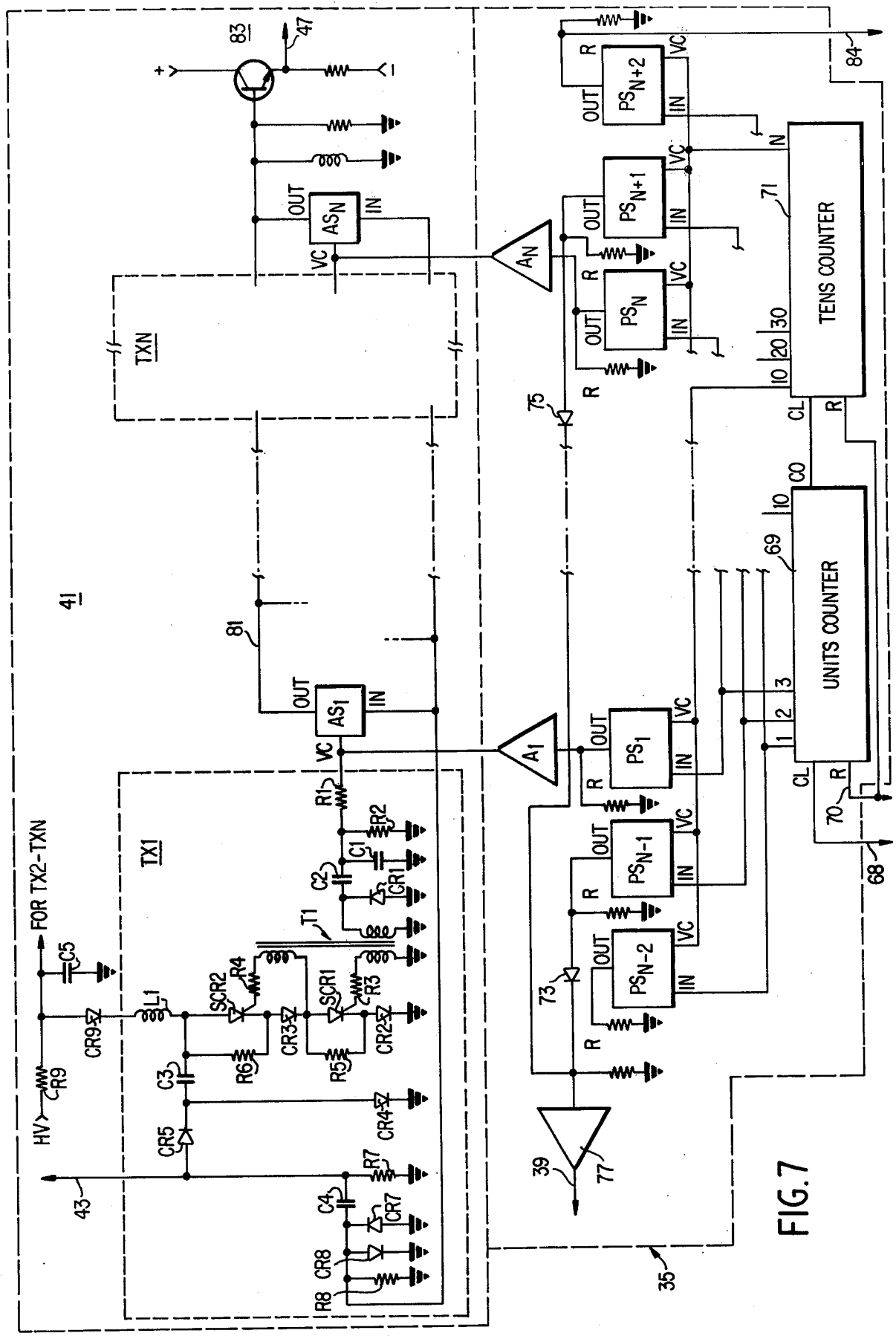

The prime embodiment of this invention is more particularly described with reference to FIG. 6 and 7 which collectively show a schematic circuit diagram of the "C" mode scan means of the ultrasonoscope of this invention. The circuits outlined in FIG. 6 and 7 by broken lines carry the same reference numbers as the blocks in FIG. 2.

Enclosed by a broken line 29 is the staircase voltage generator. A non-inverting amplifier 55 is connected to input lead 31. The output of the amplifier 55 is connected to the first input of the positive logic NOR gate 57 whose output forms the input of the positive logic NOR gate 59. The output of the amplifier 55 is also connected to the clock input CL of the D-type flip flop 61 whose set output Q comprises the second input of the NOR gate 57. The output of the NOR gate 59 is connected to the clock input CL of the 7-stage binary counter 63 and the set output Q of the D-type flip-flop 61 is connected to the reset input R of the binary counter 63. The outputs of the stages of the binary counter 63 are connected to an analog-to-digital conversion resistor ladder network 63 whose output is coupled through source follower 67 to lead 33. When each clock pulse appears on lead 31, the output of the NOR gate 57 goes low in response to a high at its inputs. The output of the NOR gate 59 is thereby caused to go high and the binary counter 63 is energized causing a voltage waveform to appear across the ladder network 65 and to be coupled through the source follower 67 to the Y-axis input of the cathode ray tube 21.

Figure 8:
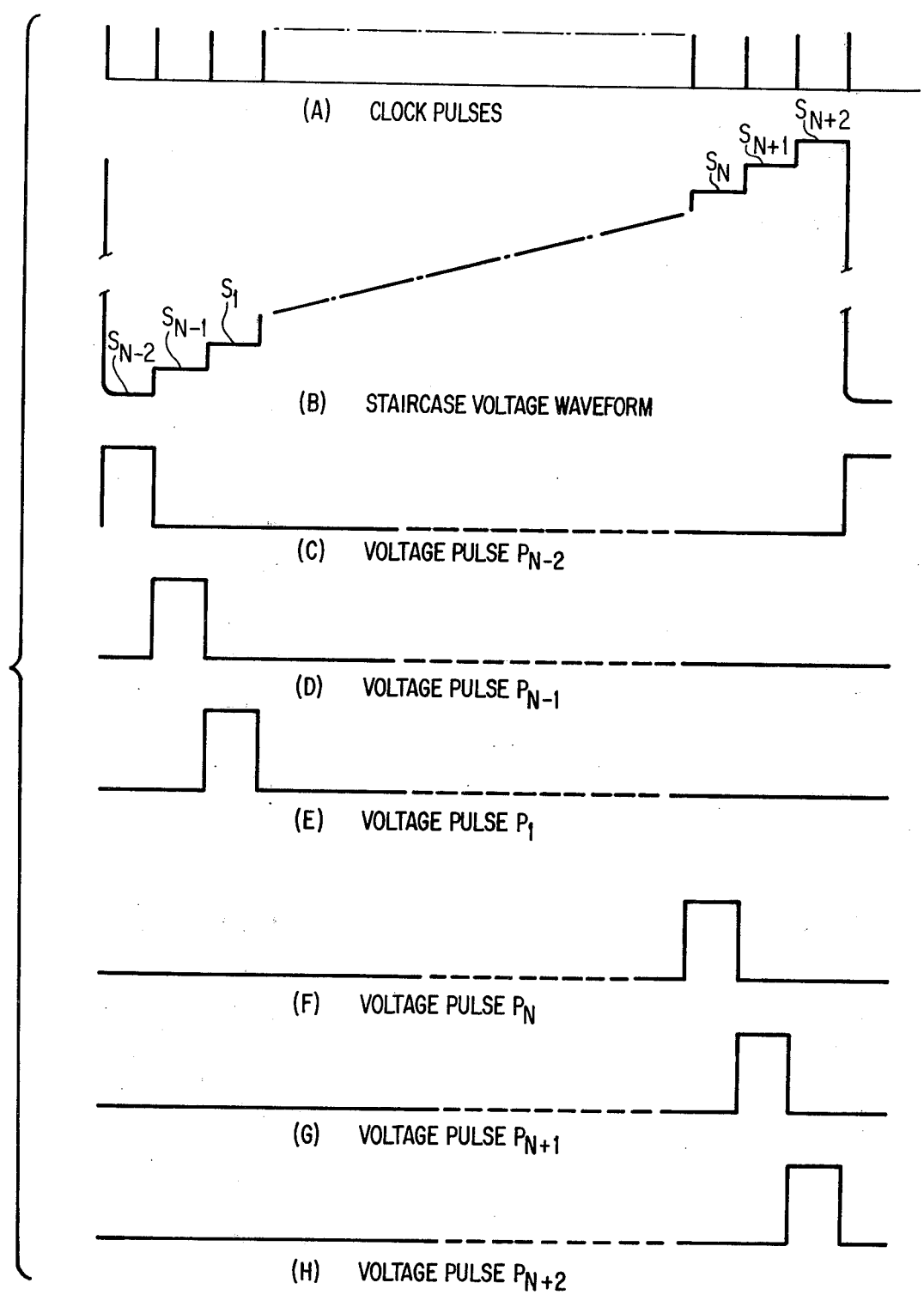
FIGS. 8(a) to (h) is a first series of waveforms produced at various points in the schematic circuit diagram of FIG. 6 and 7.

Enclosed by the broken line 35 is the sequencer. The output of the non-invertering amplifier 55 is connected by lead 68 to the clock input CL of the units decade counter 69 to start a count of units and the set output Q of the D-type flip flop 61 is connected by lead 70 to the reset input R of the units decade counter 69. A tens decade counter 71 is cascaded with the units decade counter 69 and driven thereby to indicate tens. The outputs of the stages of the units decade counter 69 are connected to the data inputs IN of the bilateral pulse switches $PS_{N-2}$ through $PS_{N+2}$, the output of the first stage being connected to every tenth pulse switch starting with $PS_{N-2}$, the output of the second stage being connected to every tenth pulse switch starting with $PS_{N-1}$, and so forth. The outputs of the stages of the tens decade counter 71 are connected to the control inputs VC of the bilateral pulse switches $PS_{N-2}$ through $PS_{N+2}$, the output of the first stage being connected to the first ten pulse switches, the output of the second stage being connected to the second ten pulse switches and so forth. The outputs OUT of the bilateral pulse switches $PS_{N-2}$ through $PS_{N+2}$ are connected to ground through the resistors R. The output of the second bilateral switch $PS_{N-1}$ and the second from last bilateral pulse switch $PS_{N+1}$ are connected through the diodes 73 and 75 to the pulse amplifier driver 77 whose output is connected by lead 39 to the depth marker generator 25. The outputs of the third through third from last pulse switches $PS_1$ through $PS_N$ are connected to the pulse amplifiers $A_1$ through $A_n$. The operation of the sequencer 35 will now be described in conjunction with FIG. 7 and the waveforms illustrated in the timing diagrams of FIG. 8. The clock pulses have a waveform as illustrated in FIG. 8(a). Let it be assumed that the units decade counter 69 and the tens decade counter 71 have been reset by a positive going pulse at their reset inputs R. When the first clock pulse appears on lead 31 the clock input CL of the units decade counter 69 goes high in response to a high at the output of the amplifier 55. A voltage pulse $P_{N-2}$ with a waveform as shown in FIG. 8(c) then appears at the output of the first stage of the units decade counter 69 and also at the data inputs IN of every tenth bilateral pulse switch starting with the first switch $PS_{N-2}$. In order for the pulse $P_{N-2}$ to pass through the switches to their outputs OUT, a positive voltage is required at the switch control inputs VC. This voltage is derived from the output of the first stage of the tens decade counter 71 and appears only for the first ten pulse switches $PS_{N-2}$ through $PS_8$. Thus only the pulse switch $PS_{N-2}$ is turned on, allowing the pulse $P_{N-2}$ to pass through to its output OUT and across the resistor R. In the meantime, the step $S_{N-2}$ of the staircase voltage waveform shown in FIG. 8(b) is generated and the staircase voltage is allowed time to settle during retrace. When the second clock pulse appears on lead 31, the clock input CL of the units decade counter 71 goes high and a voltage pulse $P_{N-1}$ with a waveform as shown in FIG. 8(d) appears at the output of the second stage of the units decade counter 69. This clock pulse also initiates step $S_{N-1}$ of the staircase voltage waveform shown in FIG. 8(b). With a positive voltage at the control input VC of the bilateral pulse switch $PS_{N-1}$ from the output of the first stage of the tens decade counter 71 pulse switch $PS_{N-1}$ is turned on next. The pulse $P_{N-1}$ passes through the switch, appears across the resistor R and is coupled through the diode 73 to the pulse amplifier driver 77. When the third clock pulse appears on lead 31, the staircase voltage is advanced another step to step $S_1$ as shown in FIG. 8(b) and a voltage pulse $P_1$ with a waveform as shown in FIG. 8(e) is caused to appear at the output of the third stage of the units decade counter 69 and at the input of pulse switch $PS_1$ and every tenth pulse switch therefrom. Only pulse switch $PS_1$ is turned on because only its control input VC voltage is high and the pulse $P_1$ passes through the pulse switch $PS_1$ to the first pulse amplifier A1. The sequence of events described for pulse $P_1$ is then repeated for each of the pulses $P_2$ through $P_8$. The voltage pulse $P_8$ is the tenth pulse event for the units decade counter 69. The next clock pulse initiates two events. The first event is that the units decade counter 69 recycles producing pulse $P_9$ at the output of its first stage. The second event is that a positive going pulse from the output CO of the units decade counter 69 is coupled to the input CL of the tens decade counter 71. This latter pulse turns off the positive voltage at the output of the first stage of the tens decade counter 71 and replaces it with a positive voltage at the output of the second stage so that the control inputs VC of the pulse switches $PS_9$ through $PS_{18}$ now are caused to go high. Pulse switch $PS_9$ is turned on and the pulse $P_9$ passes through to the ninth pulse amplifier $A_9$. The succeeding clock pulses cause the pulses $P_{10}$ through $P_N$ to be passed through the pulse amplifiers $PS_{10}$ through $PS_N$. The waveform of the voltage pulse $P_N$ is shown in FIG. 8(f), and the corresponding step $S_N$ of the staircase voltage waveform is illustrated in FIG. 8(b). When the (N+1)th clock pulse appears on lead 31, the staircase voltage is advanced to step $S_{N+1}$ as shown in FIG. 8(b) and a voltage pulse $P_{N+1}$ with a waveform as shown in FIG. 8(g) is caused to appear at the output of the corresponding stage of the units decade counter 69 and at the data input IN of the pulse switch $PS_{N+1}$. The pulse $P_{N+1}$ passes through the pulse switch $PS_{N+1}$, appears across the resistor R and is coupled through the diode 75 to the pulse amplifier driver 77. Finally, when the (N+2)th clock pulse appears on lead 31, a voltage pulse $P_{N+2}$ with a waveform as shown in FIG. 8(h) occurs at the data input IN of the pulse switch $PS_{N+2}$. The pulse $P_{N+2}$ passes through the pulse switch $PS_{N+2}$ to the direct set input S of the D-type flip-flop 79 causing its set output Q to go high, thereby resetting the binary counter 63, the units decade counter 69, and the tens decade counter 71 for a new cycle of operations.

Enclosed by a broken line 41 in FIG. 2 are the ultrasonic transmitters TXI-TXN and analog switches $AS_1$–$AS_N$. Only the details of the first transmitter TXI have been illustrated since each of the N transmitters is identical. The output of the pulse amplifier A1 is connected to the junction of the control input VC of the analog switch $AS_1$ and the resistor R1. The resistor R1 is connected by a parallel combination of the resistor R2 and the capacitor C1 to ground. Resistor R1 is also connected to ground through the capacitor C2 and the parallel combination of the diode CR1 and the primary winding of the transformer T1. A silicon controlled rectifier SCRI, shunted by the resistor R5, is connected at its gate through the resistor R3 to one of the secondary windings of the transformer T1, and at its cathode to ground through the diode CR2. A silicon controlled rectifier SCR2, shunted by the resistor R6, is connected at its gate through the resistor R4 to another secondary winding of the transformer T1, at its cathode to the anode of the silicon controlled rectifier SCR1 through the diode CR3 and at its anode to the high voltage HV through the series circuit of the coil L1, the decoupling diode CR9 and the resistor R9, and to ground through the capacitor C3 and the diode CR4. The junction of the diode CR9 and the resistor R9 is connected to ground through the capacitor C5. The junction of the capacitor C3 and the diode CR4 is connected through the diode CR5 to the junction of the first ultrasonic transducer, the resistor R7, and the capacitor C4. The capacitor C4 is connected to ground through the parallel combination of diodes CR7 and CR8 and the resistor R8, and also to the data input IN of the analog switch $AS_1$. Referring to FIGS. 7 and 9, the operation of the first transmitter will now be described, as illustrative of the operation of the N ultrasonic transmitters. The transmitter relies on capacitive discharge to fire the ultrasonic transducer. When the pulse $P_1$ with a waveform as shown in FIG. 9(a) appears at the output of the pulse amplifier A1, resistors R1 and R2 provide isolation and divide the pulse amplitude. The capacitor C1 filters out high frequency noise and the capacitor C2 differentiates the pulse. The negative portion of the differentiated pulse is clipped by the diode CR1 and the positive portion of the pulse with a waveform shown in FIG. 9(b) passes to transformer T1 causing a current to flow in its secondary windings and the silicon controlled rectifiers SCR1 and SCR2 to be triggered. Resistors R3 and R4 desensitize the gates of the silicon controlled rectifiers to RFI firing. The diodes CR2 and CR3, biased by voltage dividing resistors R5 and R6, minimize anode RFI firing of the silicon controlled rectifiers. While only two silicon controlled rectifiers are shown, it is to be understood that additional silicon controlled rectifiers can be added in cascade depending upon the magnitude of the high voltage. Capacitor C3 is charged from the high voltage HV through a charging circuit comprising the resistor R9, the diode CR9, the coil L1, the capacitor C3, and the diode CR4. When the leading edge of the pulse $P_1$ fires the silicon controlled rectifiers, the charge on the capacitor C3 is discharged through SCR1 and SCR2 via the diode CR5 and the resistor R7 in parallel with the first ultrasonic transducer. The discharge current impulse with a waveform shown in FIG. 9(c) causes the first ultrasonic transducer to radiate an ultrasonic pulse into the patient's body from the end of the transducer. The echoes picked up by the transducer are converted to electrical echo signals appearing across the resistor R7 with a waveform shown in FIG. 9(d). The electrical echo signals are capacitively coupled through the capacitor C4 to the data input IN of the analog switch $AS_1$. The diodes CR7 and CR8 are provided for clipping large signals and the resistor R8 is the input load for the analog switch. The analog switch $AS_1$ is turned on by the appearance of the pulse $P_1$ at the control input VC and the electrical echo signals are passed through the switch to a common signal bus 81 and to the base of the transistor 83 whose output is coupled to the receiver 19 by lead 47, as intensity modulating signals with a waveform shown in FIG. 9(e).

Enclosed by the broken line 49 is the bias voltage generator. The output OUT of the pulse switch $PS_{N+2}$ is connected by lead 84 to the clock input CL of the D-type flip-flop 79 whose set output Q comprises the input of the pulse amplifier 85. At the output of the pulse amplifier 85 are connected two potentiometers 87 and a source follower 89 which is connected by lead 51 to the Y input of the cathode ray tube. At the last clock pulse appearing on lead 31, the voltage pulse $P_{N+2}$ sets the D-type flip-flop 79 causing its set output Q to go high and providing an input voltage to the source follower 89. A bias voltage is thereby supplied to offset the staircase voltage at the Y input of the cathode ray tube 21.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. In a biomedical ultrasonoscope for examination of the interior of a patient's body and having "A", "M", and "C" mode scan electronic circuits whereby "A" "M" or "C" mode scan displays can be selected, the "A" and "M" mode scan electronic circuits including, in combination, a clock generator for generating clock pulses; a cathode ray tube having X, Y, and Z inputs; a sweep generator connected between the clock generator and the X axis input of the cathode ray tube for generating a cathode ray sweep signal synchronized by the clock pulses; and a receiver adapted to be connected to the Z axis input of the cathode ray tube, said "C" mode scan circuit comprising:

transducer means including a plurality of ultrasonic transducer elements arranged in a row and adapted to be positioned on the skin of the patient's body for converting a pulsed electrical signal to a pulsed ultrasonic signal, radiating the pulsed ultrasonic signal into the patient's body, picking up echoes reflected from interfaces in the patient's body and converting the echoes to electrical signals;

a plurality of analog switches equal in number to the number of ultrasonic transducer elements, each analog switch having an input and an output, each analog switch input being coupled to a respective transducer element, said analog switch outputs all being coupled to said receiver;

a plurality of transmitters, each transmitter being coupled to a respective ultrasonic transducer element for transmitting a pulsed electrical signal thereto;

a staircase voltage generator connected between the clock generator and the Y axis input of the cathode ray tube for generating a staircase voltage at said Y axis input with voltage steps synchronized by the clock pulses;

sequencer means connected to the clock generator, transmitters, analog switches, and staircase voltage generator and responsive to the clock pulses for sequentially actuating the transmitters, sequentially closing said analog switches for a predetermined gate period, and recycling said staircase voltage generator after each frame;

said sequencer means including a first counter connected to the clock generator for counting clock pulses, a second counter connected to the first counter for counting multiples of clock pulses, and a plurality of pulse switches, each pulse switch having a data input connected to the first counter, a control input connected to the second counter, and an output connected to a respective one of the plurality of transmitters.

2. The biomedical ultrasonoscope recited in claim 1 wherein each of the plurality of transmitters includes:

a capacitor having one electrode connected to a respective ultrasonic transducer;

capacitor charging means for charging the capacitor; and capacitor charging means for discharging the capacitor to transmit a pulsed electrical signal to the respective ultrasonic transducer;

said capacitor charging means including means for connecting the other electrode of the capacitor to an external high voltage source; and the capacitor discharging means including at least one silicon-controlled rectifier connected between the other electrode of the capacitor and ground, and means coupled between said silicon-controlled rectifier and one of said pulse switches for cyclically triggering said silicon-controlled rectifier and discharging said capacitor.

3. The biomedical ultrasonoscope recited in claim 1 wherein the staircase voltage generator includes:
 a binary counter connected to the clock generator and;
 an analog-to-digital conversion resistor ladder network connected between the binary counter and the Y input of the cathode ray tube.

* * * * *